Feb. 15, 1966 H. C. SWIM ETAL Plant Pat. 2,602
ROSE PLANT
Filed Dec. 1, 1964
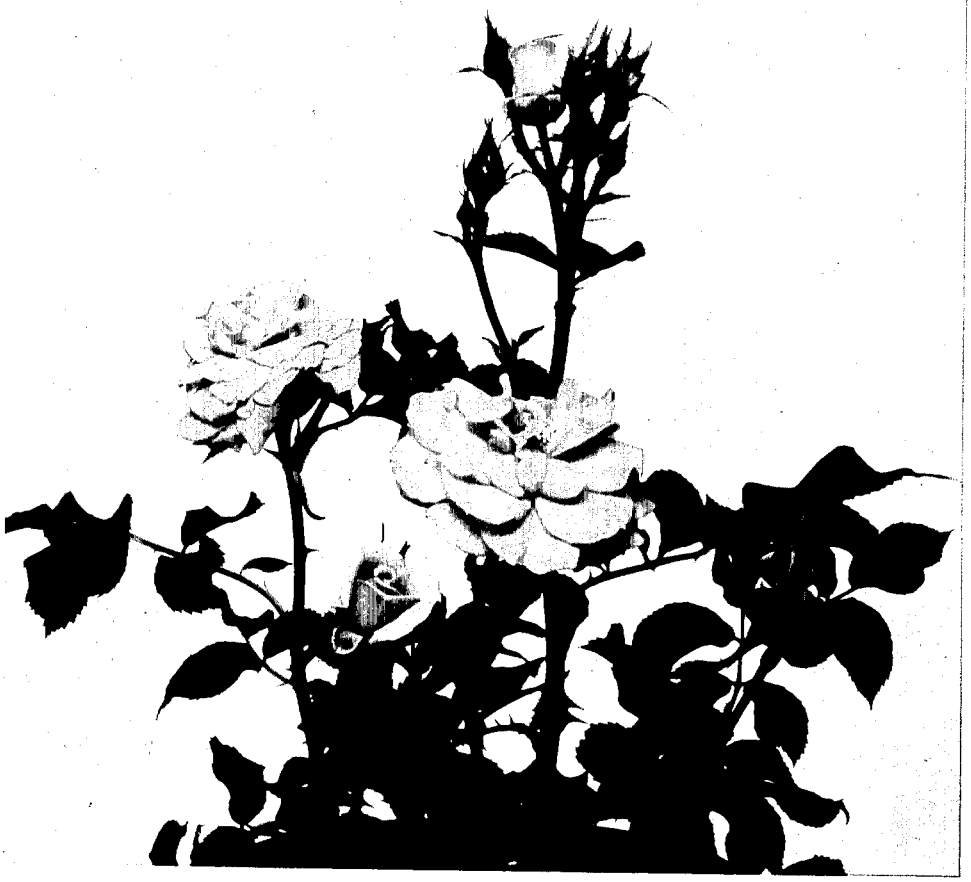
Inventors.
H. C. Swim
O. L. Weeks
By: Robb & Robb
Attorneys.

United States Patent Office

Plant Pat. 2,602
Patented Feb. 15, 1966

2,602
ROSE PLANT

Herbert C. Swim, Ontario, and O. L. Weeks, Chino, Calif., assignors to O. L. Weeks, doing business under the trade name and style of Weeks Wholesale Rose Grower, Chino, Calif.

Filed Dec. 1, 1964, Ser. No. 415,214
1 Claim. (Cl. Plt.—25)

The present invention relates to a new and distinct variety of rose plant of the floribunda class, which was originated by us by crossing the variety "Spartan" (Plant Patent No. 1,357) with the variety "Garnette" (unpatented).

As the result of this breeding, we have produced a new rose variety having the following unique combination of characteristics which are outstanding therein and which distinguish it from its parents, as well as from all other varieties of which we are aware:

(1) A low growing, compact plant habit, with only slight natural spreading, and with an unusual uniformity of growth pattern giving the plants a neat effect;

(2) A relatively continuous blooming habit, giving the effect of substantial color on the plants throughout the major portion of the growing season;

(3) A graceful urn-shaped form of the buds, said buds slowly opening to high-centered blooms of good substance and exposing the center only when the flower is full blown;

(4) A distinctive and attractive pink color of the flowers; and (5) A remarkable and complete self-cleaning habit of the flowers, usually without aid, as achieved by the timing of the abscission occuring at the base of the peduncle just as the flowers lose their ornamental usefulness, and resulting in the complete dropping of the old flowers promptly.

In comparison with its seed parent, "Spartan," our new variety has relatively shorter growth, with the over all growth habit of the plant being lower and more compact than the usual relatively long and over all tall growth of this parent; the new variety is unusually and more regular in its habit of growth, often giving the effect of containment by frequent pruning; the flowers of the new variety are substantially smaller in size than those of this parent; and the flower buds are of urn-shaped form in contrast to the pointed ovoid form of the flower buds of "Spartan."

As compared with its pollen parent, "Garnette," the plants of the new variety are substantially lower and more regular; the flower buds are of urn-shaped form in contrast to the short pointed, ovoid to globular flower buds of this parent; the flowers of the new variety are appreciably larger in size, and the flowers are pink in color, instead of the red color of the flowers of "Garnette."

A sexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Dwarf; bush; outdoor; seedling; for garden decoration.

Class: Floribunda.

Breeding: Seedling.

*Seed parent.*—"Spartan."

*Pollen parent.*—"Garnette."

Propagation: Holds its distinguishing characteristics through succeeding propagations by budding.

*Flower*

Locality where grown and observed: Chino, California.

Flowers borne: From singly to several to stem; in irregular, somewhat rounded clusters; on short, strong stems.

Quantity of bloom: Abundant, outdoors.

Continuity: From intermittent to nearly continuous.

Fragrance: Slight. Nature—tea.

Bud:

*Peduncle.*—Short; medium heavy caliper for its type; erect; smooth, except for many soft stipitate glands. Color—medium green.

*Before calyx breaks.*—Size—from medium to small for its class. Form — medium length; from pointed to urn-shaped; with foliaceous appendages on the surface of the bud; with modest foliaceous parts extending beyond the tip of the bud equal to ¼ or more of its length. Color—through Strong Reddish-Orange, Plate 7.5R 5/13 to Deep Yellowish-Pink Plate 5R 6/11.

*As calyx breaks.*—Color—from near Strong Red, plate 2.5R 5/12 to somewhat lighter than Strong Red, Plate 5R 4/12, except for a moderately prominently greenish-white spot at the base.

*As first petal opens.*—Size—medium for its class. Form — urn - shaped. Color: Outside — between Strong Purplish-Red, Plate 10RP 5/12 and Deep Pink, Plate 10RP 6/12, except for fairly prominent greenish-white spot at base which, on first petal to open may show some dilution of these colors along lower midrib; inside—ranging from Deep Pink, Plate 2.5R 6/11 through Deep Yellowish-Pink, Plate 5R 6/11 to Vivid Red, Plate 5R 5/13 over most of the petal, with moderately small but prominent greenish-white spot at base which changes quickly to the aforementioned colors.

*Opening.*—Opens up well.

Bloom:

*Size (when fully open).*—From small to medium for its class; generally from 2 to 2½ inches.

*Petalage.*—Double, but stamens not hidden; some 30 to 35 petals, plus 2 or more petaloids; arranged more or less regularly.

*Form.*—High-centered at first, but becoming flat; petals being at first very loosely rolled outward but later becoming more flat at maturity.

Petals:

*Texture.*—Thick; leathery.

*Appearance.*—Inside—satiny. Outside—from shiny to satiny.

*Shape.*—Outside—broadly orbiculate; usually entire. Intermediate—obovate-cuneate; apex very inconspicuous; usually entire. Inside—narrowly obovate-cunate; with apex occasionally notched and petal sometimes wrinkled.

This description of a newly opened flower was made from a rose grown outdoors during the month of July at Chino, California:

*Color.*—Outer petal: Outside surface — near Deep Pink, Plate 10RP 6/12, with occasional overlay of somewhat irregular pattern of strong Purplish-Red Plate 10RP 5/12, except for moderately prominently greenish-white spot at base; inside surface—between Deep Pink, Plate 10RP 6/12 and Deep Pink, Plate 2.5R 6/11, with veining faintly marked or overlayed with Vivid Red, Plate 5R 5/13, except for moderately prominent greenish-white spot at base. Intermediate petal: outside surface — between Deep Pink, Plate 10RP 6/12 and Deep Purplish-Pink, Plate 7.5RP 6/12, except for moderately prominent greenish-white spot at base; inside surface—between Deep Pink, Plate 10RP 6/12 and Deep Pink, Plate 2.5R 6/11, with veinings faintly marked or overlayed with Vivid Red, Plate 5R 5/13, except for moderately prominent greenish-white spot at base. Inner petal: outside surface—between Deep Pink, Plate 10RP 6/12 and Deep Purplish-Pink, Plate 7.5RP 6/12, except for moderately prominent greenish-white spot at base which sometimes extends briefly upward along midrib; inside surface—between Deep Pink, Plate 10RP 6/12 and Deep Pink, Plate 2.5R 6/11, with veinings faintly marked with Vivid Red, Plate 5R 5/13, except for moderately prominent greenish-white spot at base.

This description was made from a rose that was open for three days outdoors during the month of July at Chino, California:

*Color.*—Outer petal: outside surface—between Deep Purplish-Pink Plate 5RP 6/10 and Deep Purplish-Pink, Plate 7.5RP 6/12, except at base where color changes gradually to white or near white, with whitish spot appearing somewhat larger in the three-day open flower than in the newly opened flowers; inside surface — between Deep Purplish-Pink, Plate 7.5RP 6/12 and Deep Pink, Plate 10RP 6/12, except for large spot of white or near white at base. Inner petal: Outside surface — near Strong Purplish-Pink, Plate 7.5RP 7/10, except at base which is white or near white. Inside surface—near Deep Pink, Plate 10RP 6/12 at apex, but gradually shading to white or near white at base.

*General color effect.*—Newly opened flower—near Deep Pink, Plate 2.5R 6/11. Three days open—from near Deep Pink, Plate 2.5R 6/11 to between Strong Pink, Plate 2.5R 7/8 and Strong Pink, Plate 10RP 7/8.

*Behavior.*—Drop off cleanly; petals persist until color is lost, when abscission occurs at base of peduncle when both flower and peduncle drop off cleanly.

*Flower longevity.*—On bush in garden—4 days in July. Cut roses grown outdoors and kept at living room temperatures—4 days in July.

*Reproductive organs*

Stamens: From few to medium in number; arranged irregularly about pistils; often mixed with petaloids.
Filaments: From short to medium length; most with anthers. Color—from white to greenish white.
Anthers: Small; all open more or less at once. Color—yellow.
Pollon: abundant. Color—gold.
Pistils: few.
Styles: fairly even; short; medium caliper; bunched.
Stigma: translucent.
Ovaries: none observed.
Hips: does not normally set seed when grown outdoors in southern California.

Sepals: falling soon, along with petals and peduncle.
Seeds: none observed.

*Plant*

Foliage:

*Leaves.*—Compound of 3 to 7 leaflets; moderately abundant; medium size; heavy; leathery.

*Leaflets.*—Shape—lanceolate or sometimes lanceolate-cuneate. Apex — acuminate. Base — from round to cuneate. Margin—simply serrate.

*Color.*—Mature: upper surface—very dark green; under surface—light green. Young: upper surface—normal green, heavily overlaid with Deep Purplish-Red, Plate 7.5RP 3/9; under surface—light green, overlaid with Deep Purplish-Red Plate 7.5RP 3/9 principally on reticulations.

*Rachis (the supporting stem of the compound leaf).*—

Medium heavy. Upper side—grooved; a few small stipitate glands on ridges. Under side—with 2 or 3 prickles and scattered stipitate glands.

*Stipules.*—Short; moderately narrow; with short points turning out at an angle of usually less than 45°.

*Disease resistance.*—Good resistance to powdery mildew, as determined by comparison with other varieties grown under comparable cultural conditions at Chino, California.

Growth:

*Habit.*—Dwarf; bushy; upright-spreading; much-branched.

*Growth.*—Moderately vigorous.

*Canes.*—Medium caliper.

*Main stems.*—Color—bright green. Large prickles—several; medium length; straight; with short, broad base; color—brown. Small prickles—few; color—brown. Hairs—none.

*Branches.*—Color—bright green. Large prickles—several; straight; with short, broad base; color—from light green to brown, depending on maturity. Small prickles—few; color—from green to brown. Hairs—none.

*New shoots.* — Color — reddish-purple. Large prickles—few; medium length; from straight to hooked slightly downward; with short, narrow base; color — reddish-purple or purplish-red. Small prickles—few; color—from reddish-purple to light green. Hairs—none.

We claim:

A new and distinct variety of rose plant of the floribunda class, substantially as herein shown and described, characterized particularly as to novelty by the unique combination of a low growing, compact plant habit, with only slight natural spreading, and with an unusual uniformity of growth pattern giving the plants a neat effect, a relatively continuous blooming habit, giving the effect of substantial color on the plants throughout the major portion of the growing season, a graceful urn-shaped form of the buds, said buds slowly opening to high-centered blooms of good substance and exposing the center only when the flower is full blown, a distinctive and attractive pink color of the flowers, and a remarkable and complete self-cleaning habit of the flowers, usually without aid, as achieved by the timing of the abscission occurring at the base of the peduncle just as the flowers lose their ornamental usefulness, and resulting in the complete dropping of the old flowers promptly.

No references cited.

ABRAHAM G. STONE, *Primary Examiner.*